US007723506B2

United States Patent
Hartmann et al.

(10) Patent No.: US 7,723,506 B2
(45) Date of Patent: May 25, 2010

(54) *TETRAHYMENA* HEAT INDUCIBLE PROMOTERS AND THEIR USE

(75) Inventors: Marcus Hartmann, Münster (DE); Thomas Weide, Altenberge (DE); Lutz Herrmann, Herne (DE); Nadine Niebur, Münster (DE)

(73) Assignee: Cilian AG, Munster (DE)

( * ) Notice: Subject to any disclaimer, the term of this patent is extended or adjusted under 35 U.S.C. 154(b) by 0 days.

(21) Appl. No.: 11/922,348

(22) PCT Filed: Jul. 13, 2006

(86) PCT No.: PCT/EP2006/064244

§ 371 (c)(1),
(2), (4) Date: Mar. 13, 2008

(87) PCT Pub. No.: WO2007/006812

PCT Pub. Date: Jan. 18, 2007

(65) Prior Publication Data
US 2008/0261290 A1 Oct. 23, 2008

(30) Foreign Application Priority Data
Jul. 13, 2005 (EP) ................... 05106423

(51) Int. Cl.
*C07H 21/04* (2006.01)
*C12P 21/06* (2006.01)
*C12N 15/74* (2006.01)
*C12N 15/00* (2006.01)
*A01N 43/04* (2006.01)

(52) U.S. Cl. ............... 536/24.1; 435/471; 435/320.1; 435/69.1

(58) Field of Classification Search .............. None
See application file for complete search history.

(56) References Cited

OTHER PUBLICATIONS

Shang et al., "A robust inducible-repressible promoter greatly facilitates gene knockouts, conditional expression, and overexpression of homologous and heterologous genes in *Tetrahymena thermophila*", PNAS 99(6):3734-3739 (Mar. 19, 2002).
Ketola et al., "Evolution of HSP90 Expression in *Tetrahymena thermophila* (Protozoa, Ciliata) Populations Exposed to Thermally Variable Environments" Evolution, 58(4):741-748 (2004).

*Primary Examiner*—Quang Nguyen
(74) *Attorney, Agent, or Firm*—Jacobson Holman PLLC

(57) ABSTRACT

A method characterizes samples having units by monitoring fluctuating intensities of radiation emitted, scattered, and/or reflected by the units in at least one measurement volume, the monitoring being performed by at least one detection device, the method comprising the steps of: a) measuring in a repetitive mode a number of photon counts per time interval of defined length, b) determining a function of the number of photon counts per the time interval, and c) determining a function of specific brightness of the units on basis of the function of the number of photon counts.

3 Claims, 3 Drawing Sheets

Expression vector pPT HSP

Heterologous expression of reporter gene

Figure 3

Seq ID No. 1

```
agcatgcttt tcatgtact attcctaact atagcttaat gctttataca tcaaagtatg    60
aagaagacag gttttaaaaa accaaaaaat atgtttttta tttgaaaagt attatatagg   120
aataataaat gctgcataaa tactctaagt agttgataaa aaatctattt atgcaaagaa   180
aaatttagaa aaatttagaa aaacaaagaa aataattgtt attataaagc attttgttta   240
ctaagcaaaa gatataaaat ttgagataga aatatacata caagattaac gttttgtttg   300
tgctttgaaa attgaaatat ttaattatta aatctgctaa cttttttaga tatttatttg   360
ctttatttta tttttaaat ttttgcaaag tggagaaaaa tgaaacaatc aatcttttt    420
ttataaataa tataaatggt attaagccta atttttattg ctggagagtg ttattcaaat   480
atattgctga atgtggctag atggaattcg ctttggaagg aaagtgttta taaataagt    540
gatgtattat agcacattgc taattattat aaagaatgta ttggatattt aaaaattaga   600
aaataaaatt tagctgaaaa gtaagaaagc aagcaaagat atatatatat atatggagat   660
gataaaaaga taaattcgaa aaaagaaaat ttctaaagtg aaaagaatta tggatttgat   720
taaataaaaa tatttttaga atgggctgat taaagaggga tcttcgagaa tgaaatgatt   780
tagaaaaaaa gaaagaaaga ttataacatc tacaaagagt tgaagattct agaagaggag   840
gaataattag ctatcagtct tattaaaaga tatcgcaaaa caagaaatat ttttgaaatt   900
aattaaaaaa tttaaaaaac aaaagataaa aattttgcac aaaaaagcaa ttaattaaaa   960
aaaaagatat atcataagaa                                              980
```

TETRAHYMENA HEAT INDUCIBLE PROMOTERS AND THEIR USE

This is a national stage of PCT/EP06/064244 filed Jul. 13, 2006 and published in English.

FIELD OF THE INVENTION

The present invention addresses fields of recombinant molecular biology; the main topic are strong inducible promoters to be used for product synthesis in biological systems.

BACKGROUND OF THE INVENTION

Tetrahymena is a ciliated eukaryotic unicellular organism belonging to the regnum of Protozoa and bearing two nuclei, a transcriptionally silent, diploid germline micronucleus (MIC) and a transcriptionally active, polyploid somatic macronucleus (MAC). In 1923, when Nobel Laureate Andre Lwoff succeeded in growing Tetrahymena in pure culture, the basis for exploiting this Alveolate as a model organism was laid. Milestone discoveries made in Tetrahymena are the discovery of dynein motors, telomeres, RNA-mediated catalysis, telomerase and the function of histone acetyltransferases in transcription regulation. Within the last decades molecular biological techniques have been developed to alter Tetrahymena's genome and proteome: DNA transfection methods range from microinjection into the MAC, over electroporation into the MAC to biolistic bombardment of MIC and MAC. Episomal plasmids based on an rDNA-replicon are available, as well as knock-out/-in techniques based on homologous recombination. On protein level heterologous expression of related species has been performed and also endogenous proteins were silenced by a novel antisense-ribosome-technique. The biotechnological potential of Tetrahymena has been proven in numerous publications, demonstrating fast growth, high biomass, fermentation in ordinary bacterial/yeast equipment, up-scalability, existence of cheap and chemical defined media.

So far, only a few promoter active Tetrahymena DNA sequences have been characterised up to a useful extend to work with in molecular biology. These comprise the rather weak and moreover cellcycle dependent histone-[1] and beta-tubulin-promoter[2] and also heavy-metall-inducible metallothionein-promoters.[3,4] Metallothioneins, that are upregulated upon stress, are metal binding proteins playing a role in detoxification of the cell. In Tetrahymena metallothioneins are known, the promoters of which can be induced quite well by the presence of Cadmium, Copper, Zinc—induction becoming less in this order—but barely with other stress factors like peroxides or heat. As heavy metals are toxic, inhibit cell growth and lead—at higher concentrations—to cell death, a different system with less impact on the health of the system and an inducer that can be removed tracelessly would be favourable. Furthermore due to the heavy impact on the environment by heavy metal cations the disposal of contaminated media is time and resource consuming. As the financial effort in commercial bioproduction processes have to be minimal, Metallothionein promoters do not seem to be the inducible system of choice.

DESCRIPTION OF THE INVENTION

Heat shock proteins, HSPs, are evolutionary conserved stress response proteins with multiple protective functions within the cell. These proteins are ubiquitous, found in all eucaryotic organisms studied to date, and are inducible by heat stress as well as by a variety of other external agents. Thus, cells respond to these inducers, such as elevated growth temperatures, by synthesizing high levels of HSPs and coordinately reducing the rate of synthesis of other cellular proteins. HSPs are divided into several groups on the basis of size. Their occurrence in Tetrahymena has been described more than 20 years ago, too.[5] In Tetrahymena thermophila four proteins belonging to the HSP70 (accession # AAK29100) and HSP90 (accession # AAD41357) family have been described and characterized in terms of partial amino acid sequences,[6] yet the promoter active sequences have not been elucidated.

Regulation of HSPs in other systems has been studied extensively by various authors and it has been shown that promoter strength is not solely responsible for the level of protein expression: For HSP70 of Drosophila it is known that also the 3'-untranslated regions of hsp70 gene transcripts are responsible for regulating the level of protein and mRNA synthesis in the cell in both the induced and uninduced state. In the promoter region a heat shock element HSE is found 5' of the start ATG of eucaryotic heat shock genes[7]. This region includes the sequences nGAAn and nTTCn, repeated at least two times in head-to-head or tail-to-tail orientation. Number and orientation of HSEs on HSP-genes differ among species, but the binding of a positive transactivating factor, the heat shock factor (HSF) to the heat shock elements is about a hundred fold higher than that of any other known mammalian transcription factor to its respective binding site, rendering these promoters among the strongest known so far.

Therefore HSP promoters of various organisms have been used in heterologous expression systems for many proteins[8,9].

As organisms' genomes do not only vary in their codon usage but also in their AT-content, it is obvious that promoters of more distant related species will not work if exchanged among these systems. In the regnum of protists the genomes are very AT rich and as mentioned above only few promoters have been characterised. Well known and widely used promoters of yeast, E. coli, mammals and viruses have not been found to work in ciliates (own unpublished observation).

The present invention however shows that the present invention comprising promoters of the heat shock protein family of the ciliate Tetrahymena thermophila can be used for controlled foreign gene expression at high levels. It is especially preferred that the heat-inducible promoter according to the invention has the nucleotide sequence of SEQ ID NO: 1, also referred to as the HSP90 promoter, or promoter-effective fragments thereof.

The present invention is also directed to the use of the heat-inducible promoters according to the invention for the expression of homologous and/or heterologous proteins in the ciliate Tetrahymena thermophila.

It can be preferred that the heat-inducible promoter according to the invention is integrated into an expression vector containing the nucleotide sequence of the protein of interest. This vector preferably contains Tetrahymena thermophila's β-tubulin 2 terminator sequence flanking the 3' position of the coding sequence of the protein of interest.

These promoters are inducible just by heat and do not need chemical substances to be added. The induction of product is manifold. The background level of transcriptional activity is low thereby showing it to be ideal promoters for elsewhere toxic or lethal products and to serve as very good tools for conditional knock-outs and knock-ins. During fermentation the synthesis process can be stopped easily by just lowering the temperature: cells will recover and the biosynthesis can be re-induced again. This offers higher yields than other systems: As continuous fermentation is a well established method for ciliates and as thermal stress can be taken away from the culture easily, the production cycle can be repeated over and over again. In the example presented below the produced heterologous mRNAs are more stable than the endogenous HSP-mRNAs: This is achieved by the use of a 3' terminator of *T. thermophila*'s β-tubulin 2. For this reason the target gene's mRNA is still present and translated in the recovery phase of the culture. These properties of the invention lead to a new, efficient production process yet undescribed.

BRIEF DESCRIPTION OF THE FIGURES

FIG. 1 shows the used expression plasmid to verify a foreign gene's protein biosynthesis driven by different promoter active sequences. The vector consists of a bacterial backbone for amplification in *E. coli* (dark grey box), a *T. thermophila* specific origin (light grey box) for plasmid stability in *T. thermophila*, a Neomycin based selection cassette (white arrow) for identification of transformed Ciliates and an open-reading frame of a reporter protein (black arrow) followed by *T. thermophila*'s β-tubulin 2 terminator sequence (white box). Putative promoter sequences (black box) can be cloned into this vector by single cutting restriction endonucleases XhoI and EcoRV.

Figure 1:
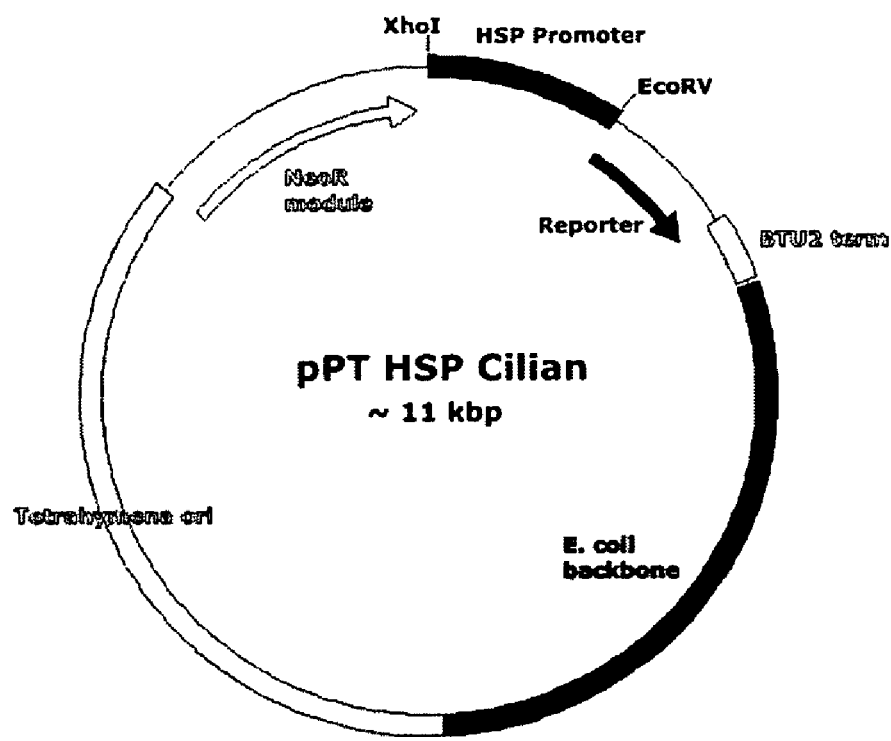
FIG. 1

Westernblot of different *T. thermophila* transformands showing expression of recombinant EGFP (enhanced green fluorescent protein) upon induction.

Lane 1: positive control, lane 2: 1,000 cells negative control (wildtype), lane 3: 1,000 cells pPT HSP90 non induced, lane 4: 1,000 cells pPT HSP90 induced for 4 h, lane 5: 1,000 cells pPT MTT non induced, lane 6: 1,000 cells pPT MTT induced for 4 h The invention will now be described in more detail by way of the following example.

FIG. 3 shows the nucleotide sequence of the HSP90 promoter (Seq Id No. 1)

EXAMPLE

The following example is provided to illustrate the embodiments of the present invention but is not intended to limit its scope.

Culturing and Transformation of *Tetrahymena*

All strains used were derived from *Tetrahymena thermophila* and have been described in detail previously. The transformation of *T. thermophila* cells was performed with modifications as published earlier.[10,11] Cultivation was carried out at 30° C. Target gene expression was induced by heat shock at 41° C. (HSPs) or by addition of 20 nM $Cd^{2+}$ (MTT1).

Cloning of HSP Promoter Regions, Coding Sequences and Vector Construction

SEQ ID NO: 1 was amplified from genomic *T. thermophila* DNA by two primers HSP90_F ATATCZCGAGAGCATGCTTTTTCATGTACTATTCC (SEQ ID NO: 2) and HSP90_R ATCCATTTGTTATGATATATCTTTTTTTTTAATTAATTGC (SEQ ID NO: 3), underlined bases bearing primer extensions. Obtained per fragment was subjected to gel electrophoresis, purified, cut by XhoI and ligated into the vector pPT Cilian, yielding a functional *Tetrahymena* vector pPT HSP90, expressing a gene coding for EGFP under control of aforementioned sequence. The 3' region of the EGFP gene's cds is flanked by the terminator sequence of *T. thermophila*'s β-tubulin 2 gene (see FIG. 1). A control vector (pPT MTT1) making use of the MTT1 promoter was constructed in the same way by the primer pair MTT1_F
ATATCTCGAGGATAAGTAATATATETAGTGCACAAT GTTTGAATG (SEQ ID NO: 4) and

MTT1_R
ATCCATTATTTTAAGTTTAGATTTATTATTTATTTTAT TAG (SEQ ID NO: 5).

Detection of EGFP

Harvested *T. thermophila* transformands were boiled in SDS-sample buffer and subjected to SDS-gel-electrophoresis. Separated proteins were blotted onto nitrocellulose membranes and EGFP was detected by a specific first antibody followed by a horseradish peroxidase conjugated secondary antibody in combination with Pierce SuperSignal on a raytest AIDA.

Inducible, Heterologous Expression of a Reporter Protein Under Control of *T. thermophila* HSP90 Promoter To test whether the identified HSP promoter is capable of expressing foreign genes, exponentially growing *T. thermophila* cell cultures transfected with pPT HSP90 were divided; one half was grown at 30° C., the other half heat shocked. Foreign gene expression driven by the MTT1 promoter was induced in pPT MTT1 transformed cells by the addition of Cadmium.

Figure 2:
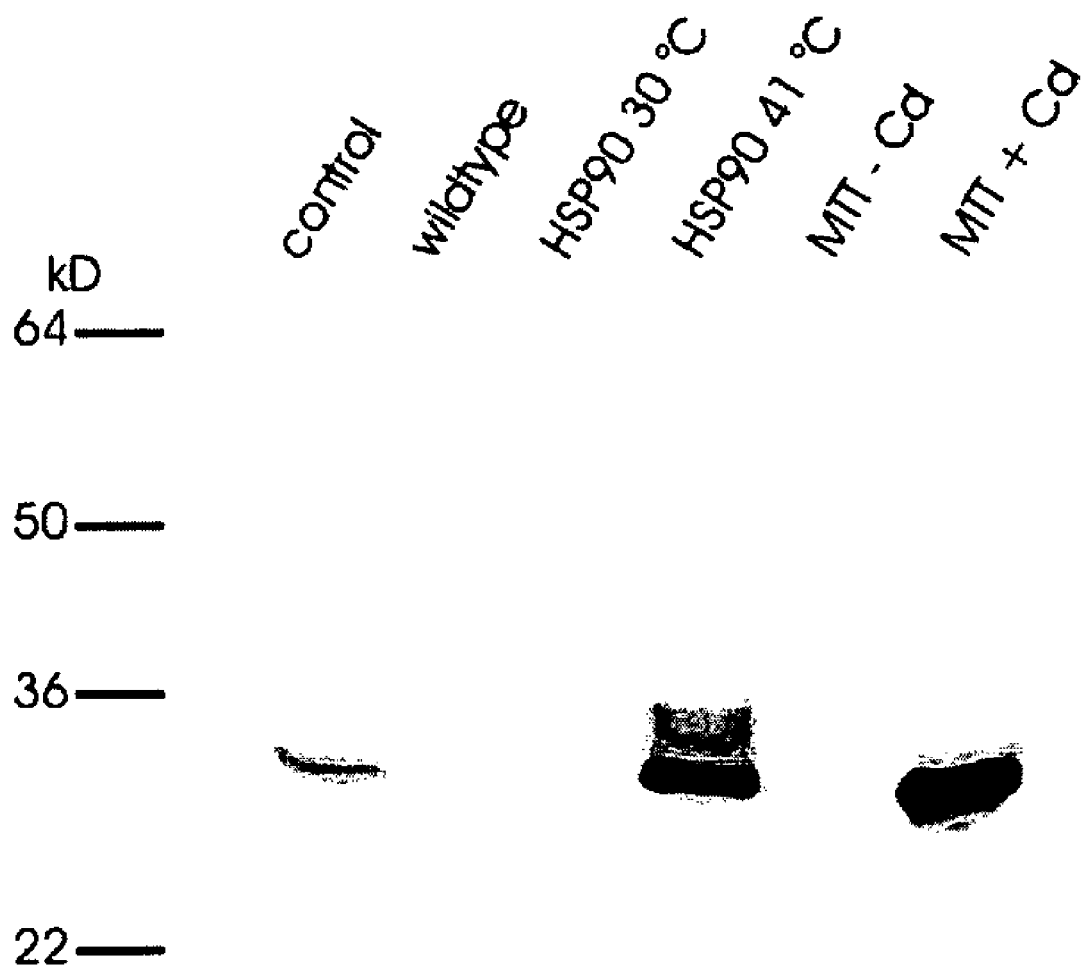
FIG. 2

FIG. 2 shows a western blot of cell lysates of these cultures. Only pPT transformed cells show detectable bands running at the same molecular weight as the control. The wildtype control (lane2) is all blank. A strong induction of expression by heat (lane 4) or by Cadmium (lane 6) is obvious compared to non induced cells (lane 3 and 5). Yet non induced cells show very low basal activity in both promoter systems.

From the data shown in FIG. 2 it can be concluded, that the promoter activity of Seq ID 1 (HSP90) can be controlled as tightly as the already published MTT1-promoter activity and that it is comparably strong.

Therefore the heat-inducible promoters according to the invention can be used in all biotechnological applications like listed for the MTT1 promoter in[12] while still being superior and favourable because of their non toxic inducibility.

REFERENCES

1. Kahn, R. W., Andersen, B. H. & Brunk, C. F. Transformation of *Tetrahymena thermophila* by microinjection of a foreign gene. *Proc. Natl. Acad. Sci. U.S.A* 90, 9295-9299 (1993).
2. Peterson, D. S., Gao, Y., Asokan, K. & Gaertig, J. The circumsporozolte protein of *Plasmodium falciparum* is expressed and localized to the cell surface in the free-living ciliate *Tetrahymena thermophila*. *Mol. Biochem. Parasitol.* 122, 119-126 (2002).
3. Shang, Y. et al. A robust inducible-repressible promoter greatly facilitates gene knockouts, conditional expression, and overexpression of homologous and heterologous genes in *Tetrahymena thermophila*. *Proc. Nat. Acad. Sci. U.S.A* 99, 3734-3739 (2002).
4. Boldrin, F., Santovito, G., Negrisolo, E. & Piccinni, E. Cloning and sequencing of four new metallothionein genes from *Tetrahymena thermophila* and *T. pigmentosa*: evolutionary relationships in *Tetrahymena* MT family. *Protist.* 154, 431-442 (2003).

5. Fink, K. & Zeuthen, E. Heat shock proteins in *Tetrahymena* studied under growth conditions. *Exp. Cell Res.* 128, 23-30 (1980).
6. Williams, N. E. & Nelsen, E. M. HSP70 and HSP90 homologs are associated with tubulin in hetero-oligomeric complexes, cilia and the cortex of *Tetrahymena*. *J. Cell Sci.* 110 (Pt 14), 1665-1672 (1997).
7. Sorger, P. K. Heat shock factor and the heat shock response. *Cell* 65, 363-366 (1991).
8. Asano, M., Nagashima, H., Iwakura, Y. & Kawade, Y. Interferon production under the control of heterologous inducible enhancers and promoters. *Microbiol. Immunol.* 32, 589-596 (1988).
9. Maggi, R. G. & Govind, N. S. Regulated expression of green fluorescent protein in *Debaryomyces hansenil*. *J. Ind. Microbiol. Biotechnol.* 31, 301-310 (2004).
10. Gaertig, J., Thatcher, T. H., Gu, L. & Gorovsky, M. A. Electroporation-mediated replacement of a positively and negatively selectable beta-tubulin gene in *Tetrahymena thermophila*. *Proc. Natl. Acad. Sci. U.S.A* 91, 4549-4553 (1994).
11. Gaertig, J. & Gorovsky, M. A. Efficient mass transformation of *Tetrahymena thermophila* by electroporation of conjugants. *Proc. Natl. Acad. Sci. U.S.A* 89, 9196-9200 (1992).
12. Gorovsky, M. A., Shang, Y. & Song, X. *Tetrahymena* Metallothionein gene promoter and its use. PCT/US02/22595. Jul. 15, 2002.
Ref Type: Patent

The invention claimed is:

1. An isolated heat-inducible promoter of the heat shock protein family of the ciliate *Tetrahymena thermophila*, whereby the promoter has the nucleotide sequence of SEQ ID NO: 1.

2. A method for expression of a homologous or a heterologous protein in *Tetrahymena thermophila*, wherein the method comprises: transforming *Tetrahymena thermophila* with an expression vector comprising (i) a coding sequence for a homologous or a heterologous protein and (ii) the heat-inducible promoter of claim 1; and culturing the transformed *Tetrahymena thermophila* to express the homologous or heterologous protein.

3. The method of claim 2, whereby the vector further comprises *Tetrahymena thermophila* β-tubulin 2 terminator sequence flanking the 3' position of the coding sequence for the protein.

* * * * *

```
SEQUENCE LISTING

<160> NUMBER OF SEQ ID NOS: 5

<210> SEQ ID NO 1
<211> LENGTH: 980
<212> TYPE: DNA
<213> ORGANISM: Tetrahymena thermophila

<400> SEQUENCE: 1
agcatgcttt ttcatgtact attcctaact atagcttaat gctttataca tcaaagtatg      60
aagaagacag gttttaaaaa accaaaaaat atgttttta tttgaaaagt attatatagg     120
aataataaat gctgcataaa tactctaagt agttgataaa aaatctattt atgcaaagaa     180
aaatttagaa aaatttagaa aaacaaagaa ataattgtt attataaagc attttgttta     240
ctaagcaaaa gatataaaat ttgagataga aatatacata caagattaac gttttgtttg     300
tgctttgaaa attgaaatat ttaattatta aatctgctaa cttttttaga tatttatttg     360 cttttatttta ttttttaaat ttttgcaaag tggagaaaaa tgaaacaatc aatctttttt     420
ttataaataa tataaatggt attaagccta atttttattg ctggagagtg ttattcaaat     480
atattgctga atgtggctag atggaattcg ctttggaagg aaagtgttta taaaataagt     540
gatgtattat agcacattgc taattattat aaagaatgta ttggatattt aaaaattaga     600
aaataaaatt tagctgaaaa gtaagaaagc aagcaaagat atatatatat atatggagat     660
gataaaaaga taaattcgaa aaaagaaaat ttctaaagtg aaaagaatta tggatttgat     720
taaataaaaa tatttttaga atgggctgat taaagaggga tcttcgagaa tgaaatgatt     780
tagaaaaaaa gaaagaaaga ttataacatc tacaaagagt tgaagattct agaagaggag     840
gaataattag ctatcagtct tattaaaaga tatcgcaaaa caagaaatat tttttgaaatt     900 aattaaaaaa tttaaaaaac aaaagataaa aattttgcac aaaaaagcaa ttaattaaaa     960
aaaaagatat atcataagaa                                                980

<210> SEQ ID NO 2
<211> LENGTH: 35
<212> TYPE: DNA
<213> ORGANISM: Artificial
<220> FEATURE:
<223> OTHER INFORMATION: HSP90_F

<400> SEQUENCE: 2
atatctcgag agcatgcttt ttcatgtact attcc                                35
```

```
<210> SEQ ID NO 3
<211> LENGTH: 40
<212> TYPE: DNA
<213> ORGANISM: Artificial
<220> FEATURE:
<223> OTHER INFORMATION: Primer

<400> SEQUENCE: 3
atccatttct tatgatatat cttttttttt aattaattgc                     40

<210> SEQ ID NO 4
<211> LENGTH: 45
<212> TYPE: DNA
<213> ORGANISM: Artificial
<220> FEATURE:
<223> OTHER INFORMATION: Primer

<400> SEQUENCE: 4
atatctcgag gataagtaat atatttagtg cacaatgttt gaatg               45

<210> SEQ ID NO 5
<211> LENGTH: 41
<212> TYPE: DNA
<213> ORGANISM: Artificial
<220> FEATURE:
<223> OTHER INFORMATION: Primer

<400> SEQUENCE: 5
atccattatt ttaagtttag atttattatt tattttatta g                   41
```